(12) United States Patent
Yamamoto (10) Patent No.: US 7,698,069 B2
(45) Date of Patent: Apr. 13, 2010

(54) METHOD FOR DESIGNING PRIMER FOR REALTIME PCR

(75) Inventor: Takamune Yamamoto, Tokyo (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 987 days.

(21) Appl. No.: 11/185,892

(22) Filed: Jul. 21, 2005

(65) Prior Publication Data

US 2006/0047442 A1    Mar. 2, 2006

(30) Foreign Application Priority Data

Sep. 1, 2004    (JP) ............................. 2004-254745

(51) Int. Cl.
*G01N 33/48* (2006.01)
(52) U.S. Cl. ..................................................... 702/19
(58) Field of Classification Search .................... 702/19
See application file for complete search history.

(56) References Cited

U.S. PATENT DOCUMENTS

2002/0038185 A1    3/2002    Kimura et al.

2004/0153254 A1    8/2004    Sagner et al.

FOREIGN PATENT DOCUMENTS

| JP | 2001-245697 | 3/2000 |
|---|---|---|
| JP | 2002-099546 | 9/2000 |
| WO | WO 02/81656 A2 | 4/2002 |
| WO | WO 03/065146 A2 | 1/2003 |

OTHER PUBLICATIONS

European Search Report dated Jan. 27, 2006.

*Primary Examiner*—Jerry Lin
(74) *Attorney, Agent, or Firm*—Stites & Harbison PLLC; Juan Carlos A. Marquez, Esq.

(57) ABSTRACT

A method for designing a primer for real-time PCR comprises retrieving a primer set using a known primer search algorithm and based on primer design conditions, visually displaying the retrieved primer set together with its splicing information and base sequence, narrowing the primer set using narrowing conditions, and visually displaying a narrowed primer set together with its splicing information and base sequence.

4 Claims, 9 Drawing Sheets

METHOD FOR DESIGNING PRIMER FOR REALTIME PCR

BACKGROUND OF THE INVENTION

1. Field of the Invention

The present invention relates to a method for designing a primer in a real-time PCR (to be hereafter referred to as RT-PCR).

2. Background Art

As one of the means for comparing the amount of expression of genes, a method whereby the amount of mRNA accumulated in cells is determined is widely employed. RT-PCR is widely utilized in recent years as a method for measuring the amount of accumulated mRNA. In a general procedure involving RT-PCR, the accumulated amount of mRNA is measured as follows. Samples grown under different conditions, or samples of different series grown under identical conditions are prepared, and mRNA is extracted from a tissue of concern. Using the thus extracted mRNA as a template, PCR is conducted under conditions including a primer set specific to a target gene and a fluorescent dye that binds to double strands to emit color. The fluorescent intensity in a reaction solution is measured in parallel with the reaction, whereby the number of nucleic acids in the double strands is measured. Based on the increase in fluorescent intensity, the amount of amplification product is determined.

PCR is a highly sensitive process and is theoretically capable of performing amplification even from a few copies of template. If genomic DNA is mixed in the extracted mRNA, amplification even occurs based on the genomic DNA as a template. In this case, PCR products would include both those based on mRNA as a template and those based on genomic DNA as a template. As a result, the amount of mRNA would not be accurately measured.

Figure 1:
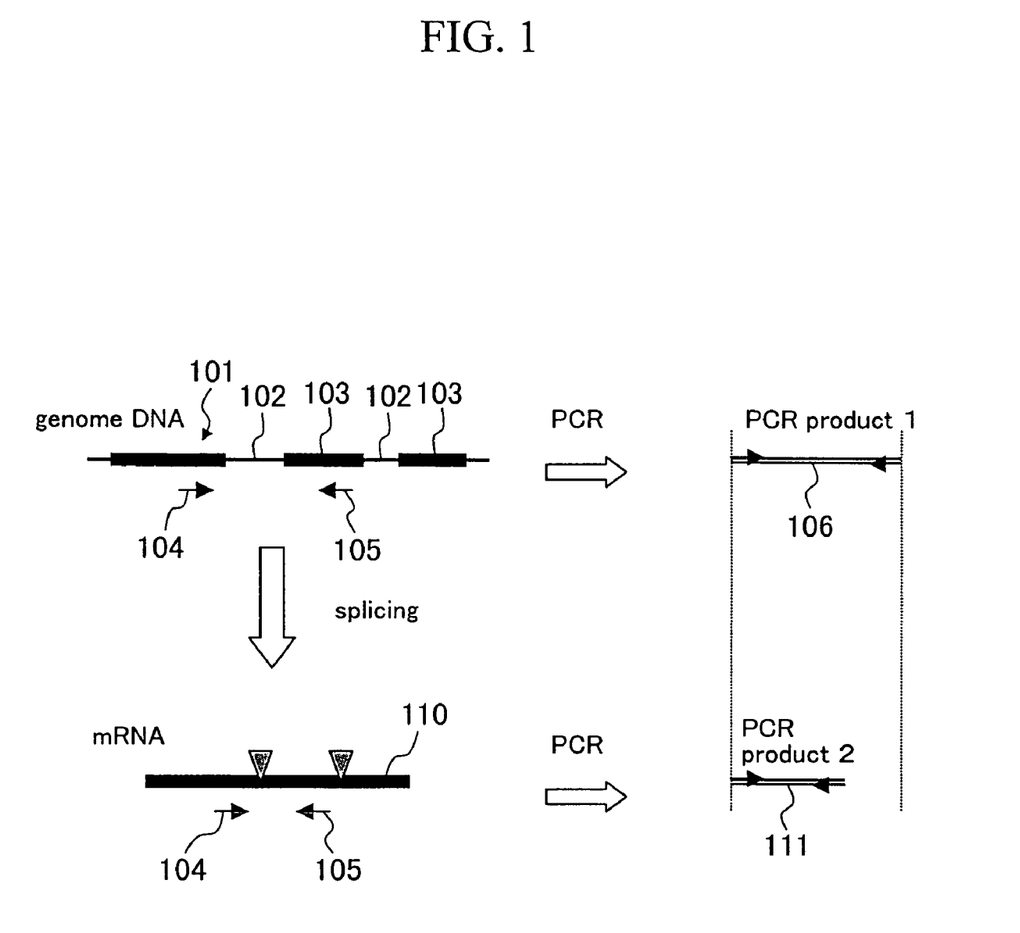
FIG. 1 illustrates the relationship between types of templates and the length of PCR products.

With reference to FIG. 1, the relationship between the types of template and the length of PCR products is described. In a eukaryotic experimental system, when splicing a target gene, individual primers are designed on different exons. Genomic DNA 101 has intron 102 and exon 103. Primer 104 on the sense strand side is represented by an arrow pointing to the right, and primer on the nonsense strand side by an arrow pointing to the left. When genomic DNA 101 is used as a template, a PCR product 106 would include an intron portion. When mRNA 110 is used as a template, a PCR product 111 would not include an intron portion and would therefore be shorter than when genomic DNA is used as a template. Based on the lengths of the PCR products, amplification products based on genomic DNA as a template can be distinguished from amplification products based on mRNA as a template. For this purpose, a method is required for designing a primer on exons with an intron portion disposed between them.

Furthermore, when the measured mRNA amount is compared between different samples, an analytical curve must be prepared. Theoretically, if the temperature cycle in PCR differs by one cycle, the amount of template doubles. However, in practice, this varies from one experiment to another, depending on experimental conditions, target base sequence, and primer sequence. Thus, for comparing the mRNA amount between different samples, a PCR product is prepared that includes only the target base sequence of the primer, and then an analytical curve is prepared using the dilution series of DNA that contains only the target base sequence as a template. Accordingly, a method is required for designing a primer for preparing a template that only contains the target base sequence of the primer for measuring the mRNA amount.

Patent Document 1: JP Patent Publication (Kokai) No. 2001-245697 A

SUMMARY OF THE INVENTION

In experiment utilizing RT-PCR, an experiment-supporting functionality is required for designing a primer at positions with intron disposed between them. To realize such functionality, the following three conditions must be met:

(1) The genomic base sequence and mRNA base sequence of a target gene have been determined by prior studies.

(2) The primer can be designed at positions that do not include a splicing site on exons sandwiching an intron with an experimentally measurable length.

(3) The information about the designed primer can be displayed in an easy-to-understand manner for the preparation of an analytical curve and for determination purposes, thereby facilitating comparison and analysis.

It is therefore an object of the invention to provide a method whereby the aforementioned conditions 2 and 3 can be satisfied and whereby a primer for real-time PCR can be easily designed.

The invention provides a method for designing a primer for real-time PCR, comprising the steps of:

entering the base sequence data for a target gene;

determining whether or not said base sequence data contains splicing information;

acquiring splicing information if it is determined in said determination step that splicing information is not contained;

entering primer design conditions for the designing of a primer at positions of exon with intron disposed between them;

retrieving a primer set using a known primer search algorithm and in accordance with said primer design conditions;

visually displaying a retrieved primer set, together with said splicing information and said base sequence;

entering a condition for narrowing the displayed primer set; and visually displaying said primer set narrowed using the narrowing condition, together with said splicing information and base sequence.

DESCRIPTION OF THE PREFERRED EMBODIMENTS

Figure 2:
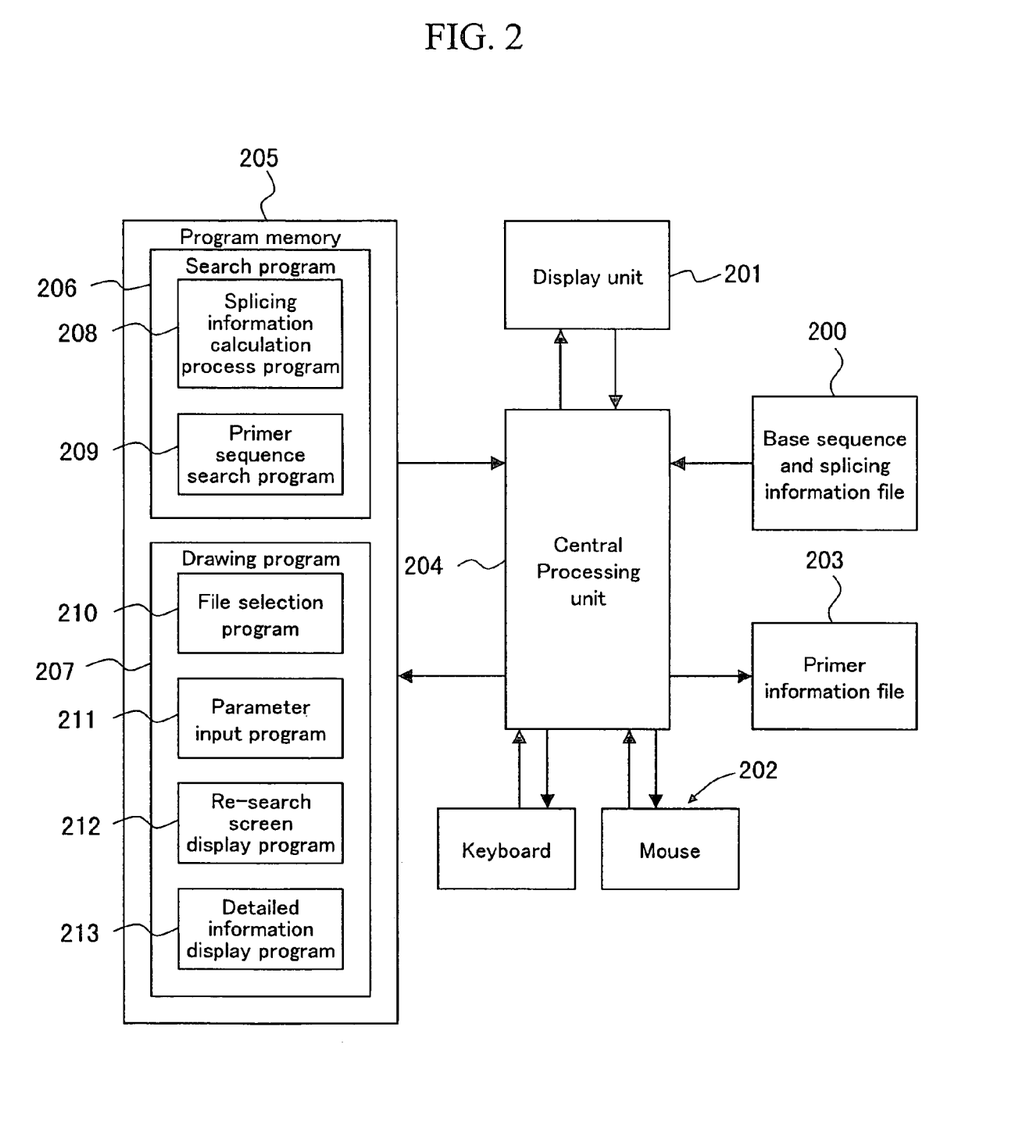
FIG. 2 shows a block diagram of a RT-PCR primer designing apparatus of the invention.

An embodiment of the invention is described in the following with reference to the drawings. FIG. 2 shows a block diagram of a RT-PCR primer designing apparatus according to the invention. The RT-PCR primer designing apparatus of the present embodiment includes a file 200 containing the base sequence data about a target gene and splicing information; a parameter input screen for primer designing purposes; a display unit 201 for displaying the information about the primer that has been designed; input means 202 including a keyboard and mouse; a file 203 containing the designed-primer information; a central processing unit 204; and a program memory 205 in which various programs are stored.

The program memory 205 stores search programs 206 and drawing programs 207. The search programs 206 include a splicing information calculation program 208 for calculating splicing information, and a primer sequence search program 209 for a primer designing process, namely, for retrieving a primer sequence. The drawing programs 207 include a file selection program 210 for displaying a screen for the entry of a file to be selected as a template; a parameter input program 211 for displaying a screen for the entry of primer designing parameters (conditions); a re-search screen display program 212 for displaying a screen on which primer search results can be narrowed; and a detailed information display program 213 for displaying a detailed information screen for an mRNA amount measuring primer. The primer designing process is carried out in the wizard format. When any of these programs is run, a dialog-format screen is displayed. When a process is initiated by the primer designing apparatus of the present embodiment, the file selection program 210 is initially run, whereby a screen shown in FIG. 3 is displayed.

Figure 3:
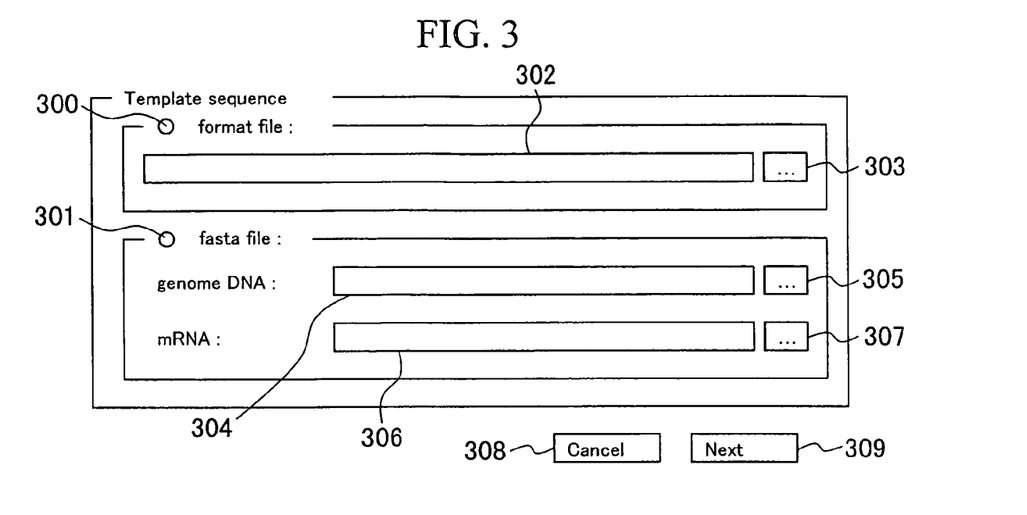
FIG. 3 shows an example of a screen for the entry of data.

FIG. 3 shows an example of the file-selection screen that is displayed when the file selection program 210 is run. The screen incorporates a radio button 300 for selecting a file with annotation information as a template, and another radio button 301 for selecting a file without annotation information as a template. As an example of the file with annotation information, a published gene database file can be mentioned. As an example of the file without annotation information, a genomic DNA and mRNA base sequence data prepared by the user can be mentioned. The user selects either one of the radio buttons. The selected field is placed in an input-activated state. The field that has not been selected is placed in an input-deactivated state.

Selecting the button 300 activates a button 303 for displaying a list of files in the published gene database for clicking. When the button 303 is clicked and a file is selected, a path of the selected file is displayed in a text box 302.

Selecting the button 301 activates a button 305 for displaying a list of the files of the genomic DNA base sequence, and a button 307 for displaying a list of the mRNA base sequence files, for clicking. When the button 305 or 307 is clicked and a file is selected, the path of the selected file is displayed in a text box 304 or 306. Alternatively, the user may directly enter a path in the text box 302, 304, or 306.

When the process is to be terminated, a cancel button 308 is depressed. The process can be continued by depressing a button 309.

Figure 4:
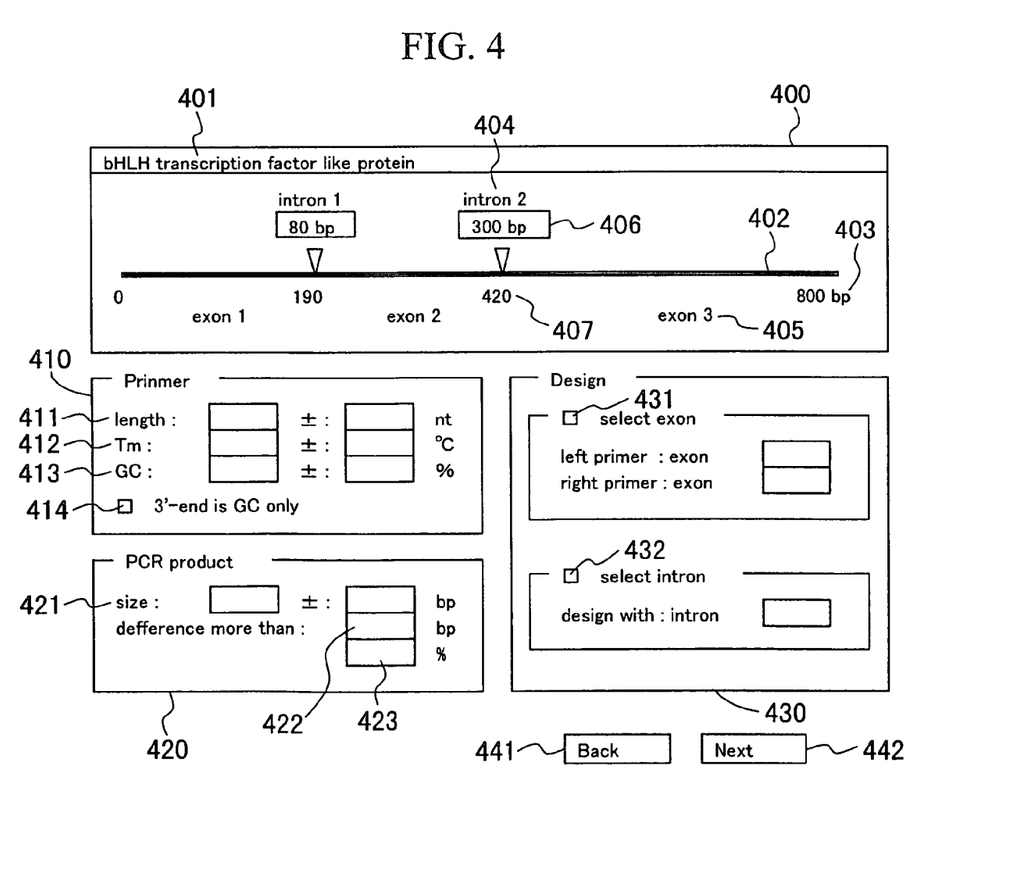
FIG. 4 shows an example of a screen for the entry of primer designing parameters.

If the button 309 is depressed when the button 300 has been selected, the parameter input program 211 is activated, whereby the screen shown in FIG. 4 is displayed. If the button 309 is depressed when the button 301 has been selected, the splicing information calculation program 208 is activated, whereby the splicing information is acquired. After the splicing information is thus acquired, the parameter program 211 is run, whereby the screen shown in FIG. 4 is displayed.

In the above example, it is assumed that the files in the published gene database contain splicing information while the genomic DNA and mRNA base sequence data prepared by the user do not contain splicing information. However, there are cases in which published gene databases do not contain splicing information and the splicing information is obtained from the genomic DNA sequence data and mRNA base sequence data prepared by the user.

FIG. 4 shows an example of a screen for the entry of primer designing conditions (parameters), which is displayed when the parameter input program 211 is run. The screen includes a field 400 for displaying splicing information; a field 410 for the entry of primer search conditions; a field 420 for the entry of PCR product conditions; and a field 430 for designating design options. The field 400 shows a gene name 401 and splicing information in a schematic fashion. The splicing information includes schematic representations of mRNA base sequence 402, full length 403, intron number 404, exon number 405, the length of intron sequence removed by splicing 406, and position 407 of binding by splicing.

The field 410 includes the length and value width 411 of a designed primer; Tm value 412, GC content 413, and a check box 414 for designating an option for selecting only those primer candidates whose 3' terminal is G or C. The field 420 includes the length and value width 421 of PCR product obtained by the designed primer; a text box 422 for the entry of a minimum value of the difference in length of PCR products [The length of PCR product when genomic DNA is used as template—the length of PCR product when mRNA is used as template]; and a text box 423 for the entry of a minimum value of intron ratio [The length of intron/the length of PCR product when mRNA is used as template×100]. The user makes an entry in either one of the two text boxes 422 and 423.

The field 430 includes a check box 431 for designating the exon number on the left and right sides for designing each primer; and a check box 432 for designating the intron number displaced between exons. The two check boxes 431 and 432 may be selected simultaneously. When a plurality of exon numbers or intron numbers are entered, a comma "," may be inserted between the individual numbers. The screen further includes a button 441 for returning to the previous data input screen shown in FIG. 3, and a button 442 for proceeding to the next process. When the button 442 is depressed, the primer sequence search program 209 is initiated. When the primer sequence search program 209 is being run, a screen shown in FIG. 5 is displayed.

Figure 5:
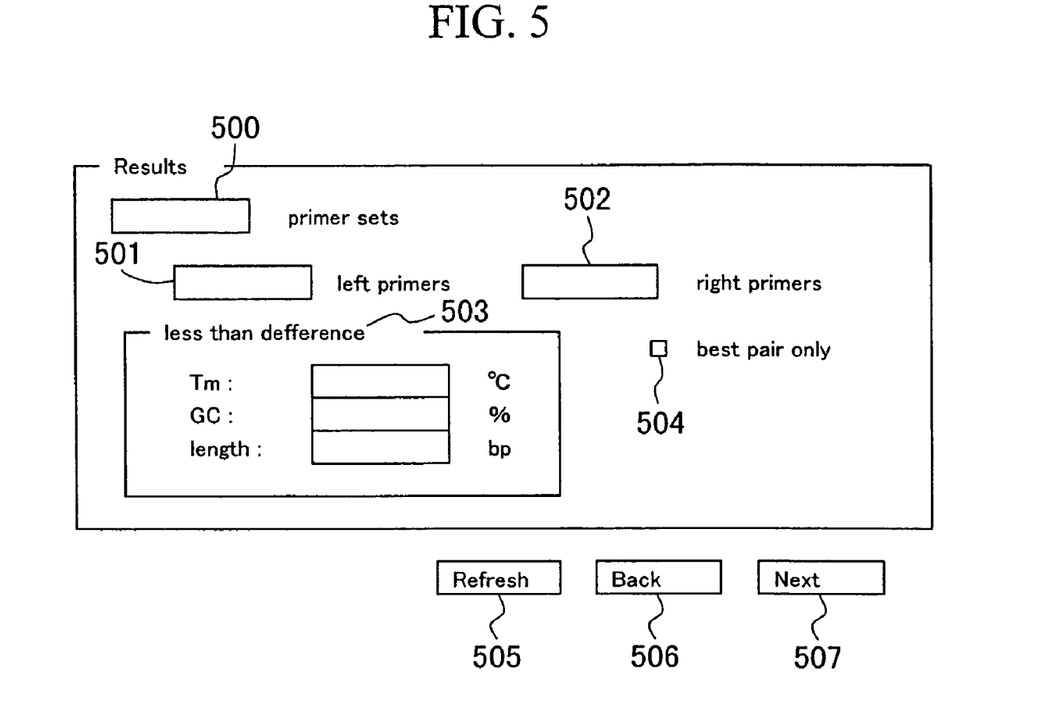
FIG. 5 shows a screen for narrowing display results.

FIG. 5 shows an example of the screen that is displayed when the re-search screen display program 212 is being run, for the entry of conditions for narrowing the search results. The screen includes a text box 500 for displaying the total number of primer sets that have been retrieved; a text box 501 for displaying the total number of retrieved primers on the sense strand side; a text box 502 for displaying the total number of retrieved primers on the nonsense strand side; a field 503 for the entry of parameters for narrowing the displayed results; and a check box 504 for designating an option for displaying only those primers among the primer combinations that most well correspond to conditions. The field 503 includes individual areas for the Tm value, GC content, and the length of primer.

The screen further includes a refresh button 505, a button 506 for returning to the dialog screen for designating the primer designing conditions shown in FIG. 4; and a button 507 for proceeding to the next process. If the refresh button 505 is depressed after narrowing conditions have been entered in the field 503, only those primer information is extracted that correspond to the conditions, and the information is reflected on the values in the text boxes 500, 501, and 502. When the button 507 is clicked, the detailed information display program 213 is initiated, and a screen shown in FIG. 6 is displayed.

Figure 6:
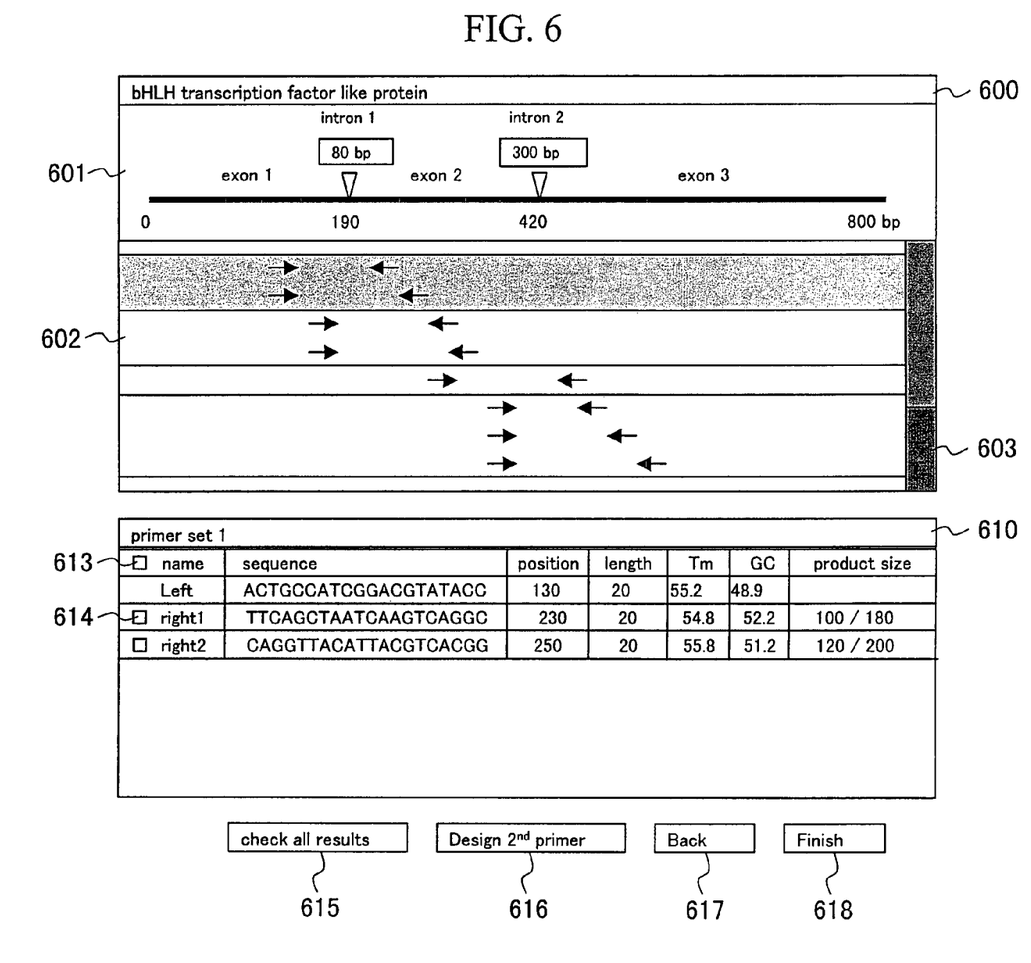
FIG. 6 shows a screen for displaying measurement primer results.

FIG. 6 shows an example of the screen for displaying the detailed results of designing an mRNA amount-measuring primer, which is displayed when the detailed information display program 213 is run. This screen includes a field 600 for displaying primer information in a schematic fashion, and a field 610 for displaying the detailed information about the primer set selected in the field 600. The field 600 includes, in addition to the field 601 for displaying the splicing information about the target gene, a field 602 for displaying the position information regarding the primer set. With regard to the primer set, a primer set herein refers to a plurality of primers on the nonsense strand side relative to one primer on sense strand side. If the position information regarding a primer set cannot be displayed all at once, the display area is moved using a scroll bar 603.

When a line corresponding to a particular primer set is selected in the field 602, the detailed information about that primer set is displayed in the field 610. The field 610 shows the primer name; primer base sequence; position on the mRNA base sequence where complementary binding of the 5' terminal of primer occurs; primer length; Tm and GC contents of primer; and the length of PCR product in a case where mRNA is used as template and a case where genomic DNA is used as template.

The field 610 includes a check box 613 for selecting all of the primer sets and a check box 614 for selecting a single primer set. The screen also includes a button 615 for checking all of the primer sets; a button 616 for proceeding to the primer design step for preparing a template for creating an analytical curve; a button 617 for returning to the previous process; and a button 618 for ending the primer designing and outputting the information about a selected primer to the file 203.

The button 616 can be clicked when the check box 614 is selected. Specifically, a set of primers is selected when preparing a template for the creation of an analytical curve. When the button 616 is clicked, a condition excluding an area sandwiched by a set of primers selected in the check box 614 is added in the parameters for primer design, and then primer designing starts. Thereafter the screen shown in FIG. 5 for narrowing the display results is displayed again, and the above-described procedure is performed. When the button 507 in the screen of FIG. 5 is depressed, a screen for displaying the result of the primer for preparing an analytical curve-creating template is displayed, as shown in FIG. 7.

Figure 7:
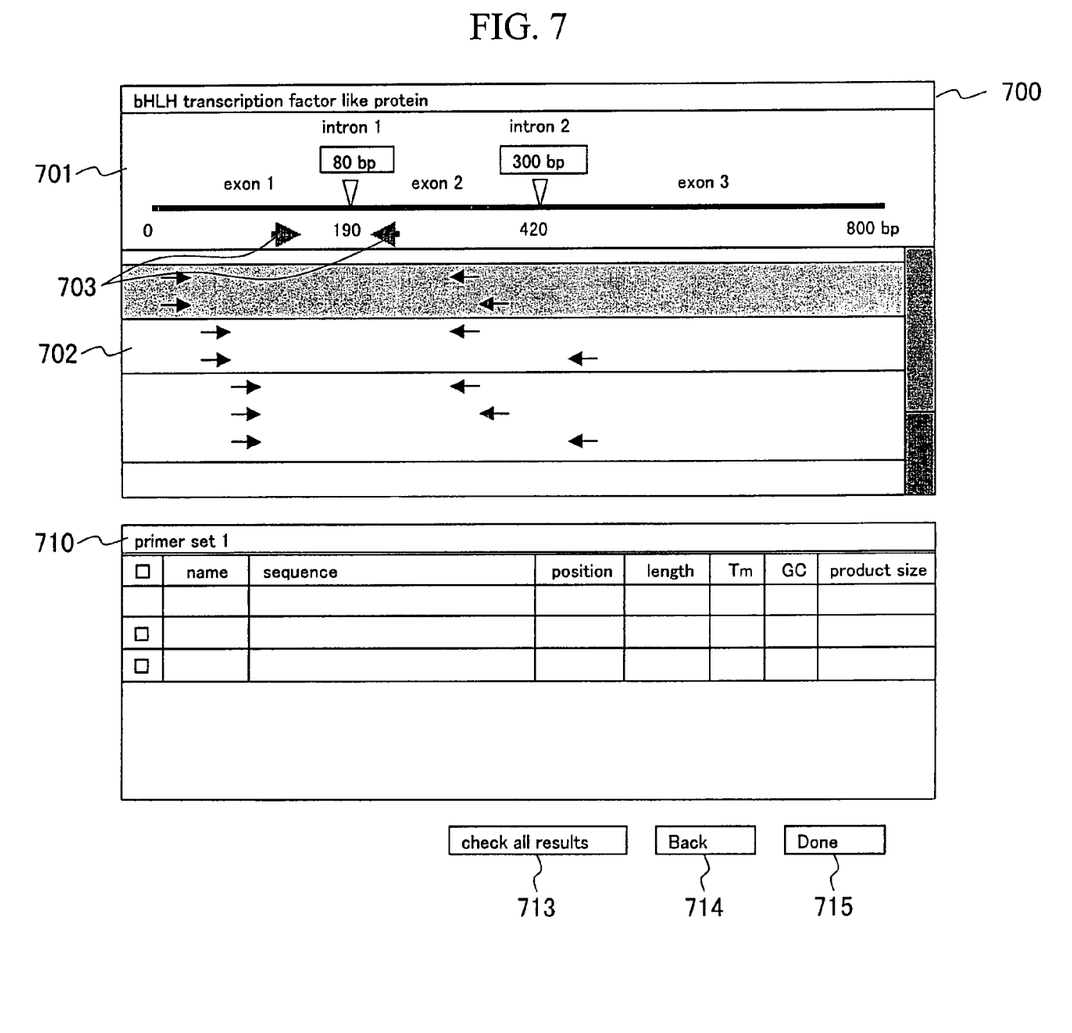
FIG. 7 shows the result of designing a primer for preparing a template for creating an analytical curve.

FIG. 7 shows an example of the screen for displaying the result of designing a primer for preparing an analytical curve-creating template. The screen includes a field 700 for displaying primer information in a schematic fashion, and a field 710 for displaying the detailed information about the primer set selected in the field 700. In the present example, the field 701 for displaying the splicing information shows the position information 703 for the measurement primer set selected in the check box 614 in the screen shown in FIG. 6. The screen also includes a button 713 for checking all of the primer sets; a button 714 for returning to the previous process; and a button 715 for ending the primer designing and adding the information about the selected primer to the file 203. When a line corresponding to a set of primers is selected in the field 702 and then the button 715 is depressed, the result of primer designing for preparing the selected template for analytical curve creating purposes is added to the selected measurement primer information. The screen then returns to the screen shown in FIG. 6.

Figure 8:
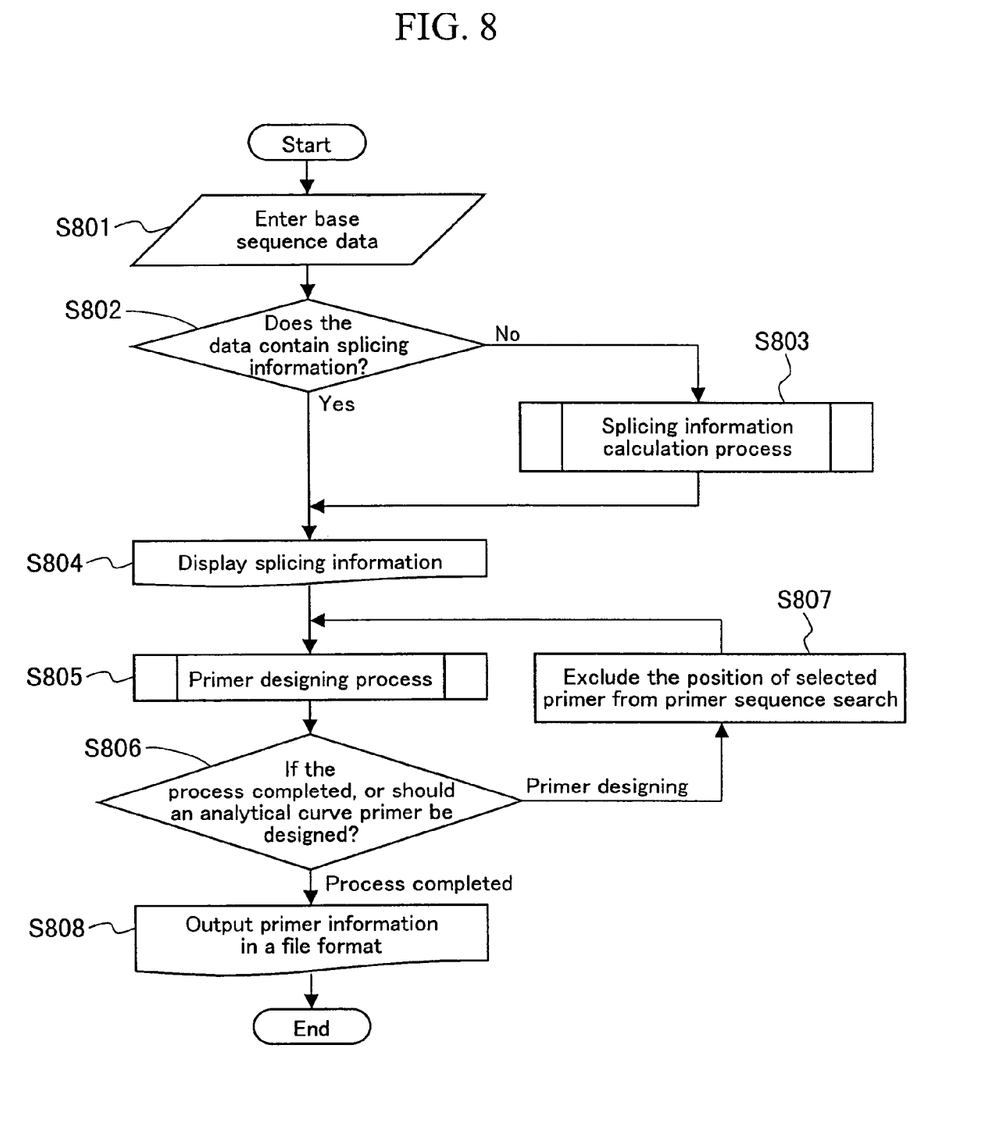
FIG. 8 shows a flowchart outlining the processes performed in accordance with the invention.

FIG. 8 shows an outline of the processes performed by the primer designing apparatus of the invention. At step S801, base sequence data is entered. At step S802, it is determined whether the entered base sequence data contains splicing information. As described above, when the radio button 300 for selecting the use of a file in a published gene database as a template of FIG. 3 has been clicked, the base sequence data includes splicing information, so that the routine proceeds to step S804. On the other hand, when the radio button 301 has been clicked to select the use of the base sequence data for genomic DNA and mRNA prepared by the user as a template of FIG. 3, the base sequence data does not contain splicing information, so that the routine proceeds to step S803. At step S803, a process for calculating the splicing information is performed, of which the details will be described with reference to FIG. 9. At step S804, the screen of FIG. 4 is displayed, which includes the field 400 for displaying the splicing information, and fields 410, 420, and 430 for the entry of primer design conditions (parameters). At step S805, a primer design process is carried out based on the thus entered parameters, of which the details will be described with reference to FIG. 10. At step S806, it is determined whether or not the primer designing for preparing an analytical curve-creating template is to be conducted. If the primer designing for preparing an analytical curve-creating template is to be conducted, the area sandwiched by the measurement primer set selected in the check box 614 in the screen of FIG. 6 is excluded from the processed object, and the primer designing process is performed again. At step S808, information about the primer that has been designed is outputted to the file 203, and the routine ends.

Figure 9:
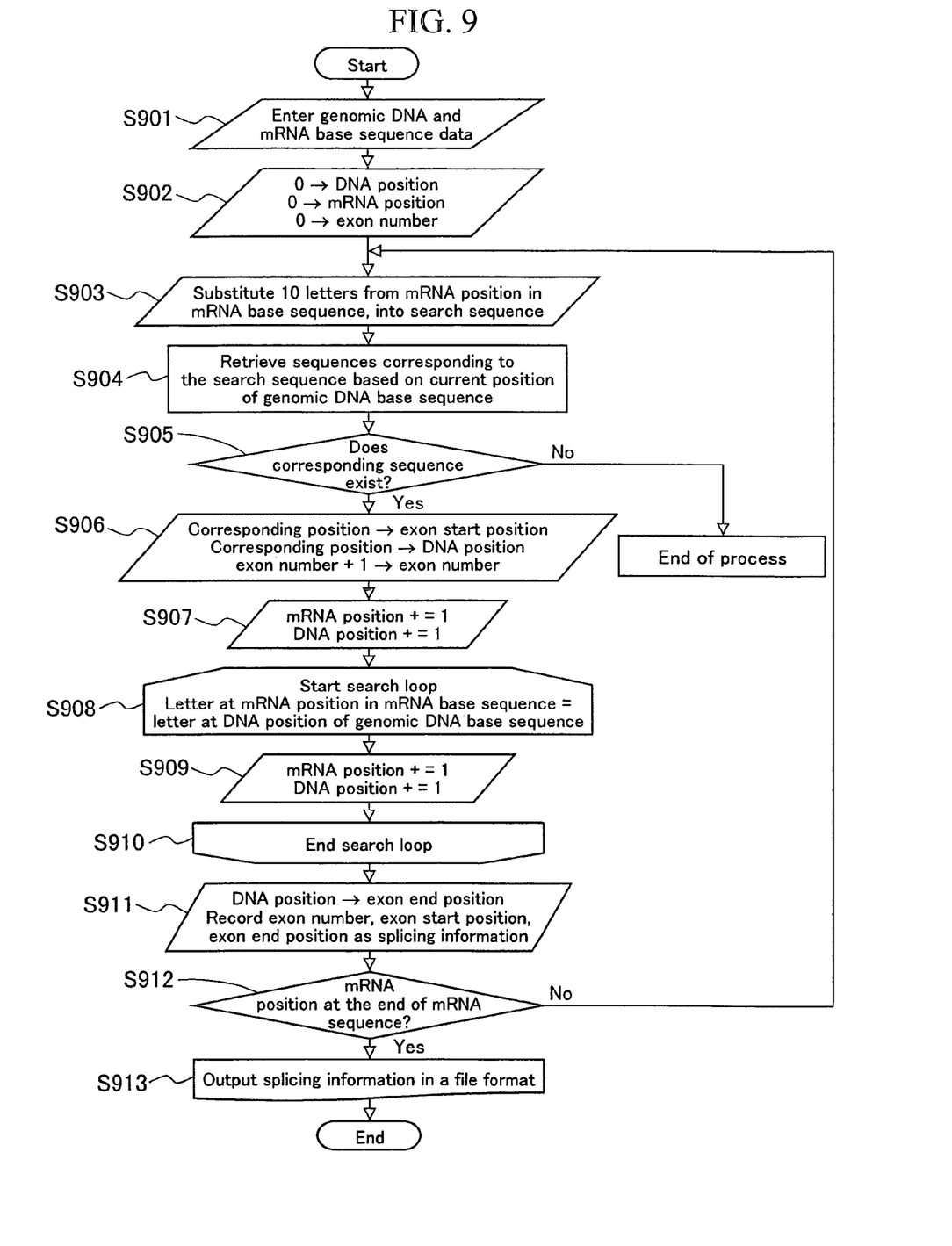
FIG. 9 shows a flowchart of the processes for calculating splicing information.

FIG. 9 shows an outline of the process for calculating the splicing information at step S803. The process is carried out by the pricing information calculating process program 208. At step S901, genomic DNA and mRNA base sequence data are entered. At step S902, the base sequence is processed as a character string, and an initial value of zero is substituted in the variable "DNA position" and the variable "mRNA position." An initial value of zero is also entered in the variable "exon number," which counts the number of exons. At step S903, 10 characters from the "mRNA position" in the mRNA base sequence are substituted in a character string "Searched sequence." At step S904, sequences corresponding to the genomic DNA base sequence are retrieved from the "DNA position." The mRNA base sequences obtained by splicing are all included in the genomic DNA base sequence. At step S905, it is determined if there is a corresponding sequence. If not, the input data is erroneous, and therefore the process terminates. If there is a corresponding sequence, the subscript of the corresponding letter in the genomic DNA base sequence is used as the corresponding position, and is substituted into the variables "exon start position" and "DNA position" at step S906. Because there is exon in this case, the "exon number" is incremented. At step S907, the "mRNA position" and "DNA position" are incremented.

Steps S908 to S910 constitute a search loop, in which the letter following the "DNA position" in the genomic DNA base sequence and the letter in the "mRNA position" in the mRNA base sequence are compared. If they correspond, the "mRNA position" and "DNA position" are incremented at step S909, and then it is determined once again if they correspond. The comparison is repeated until they do not correspond. When they cease to correspond, this means the end of exon, and therefore the routine advances to step S911.

At step S911, the "DNA position" is substituted into the variable "exon end position," and the "exon number," "exon start position," and "exon end position" are added to the splicing information.

At step S912, it is determined whether the "mRNA position" is at the end of the mRNA sequence. If the "mRNA position" is not at the end of the mRNA sequence, the routine returns to step S903. If the "mRNA position" is at the end of the mRNA sequence, the routine advances to step S913 where the splicing information is outputted.

Figure 10:
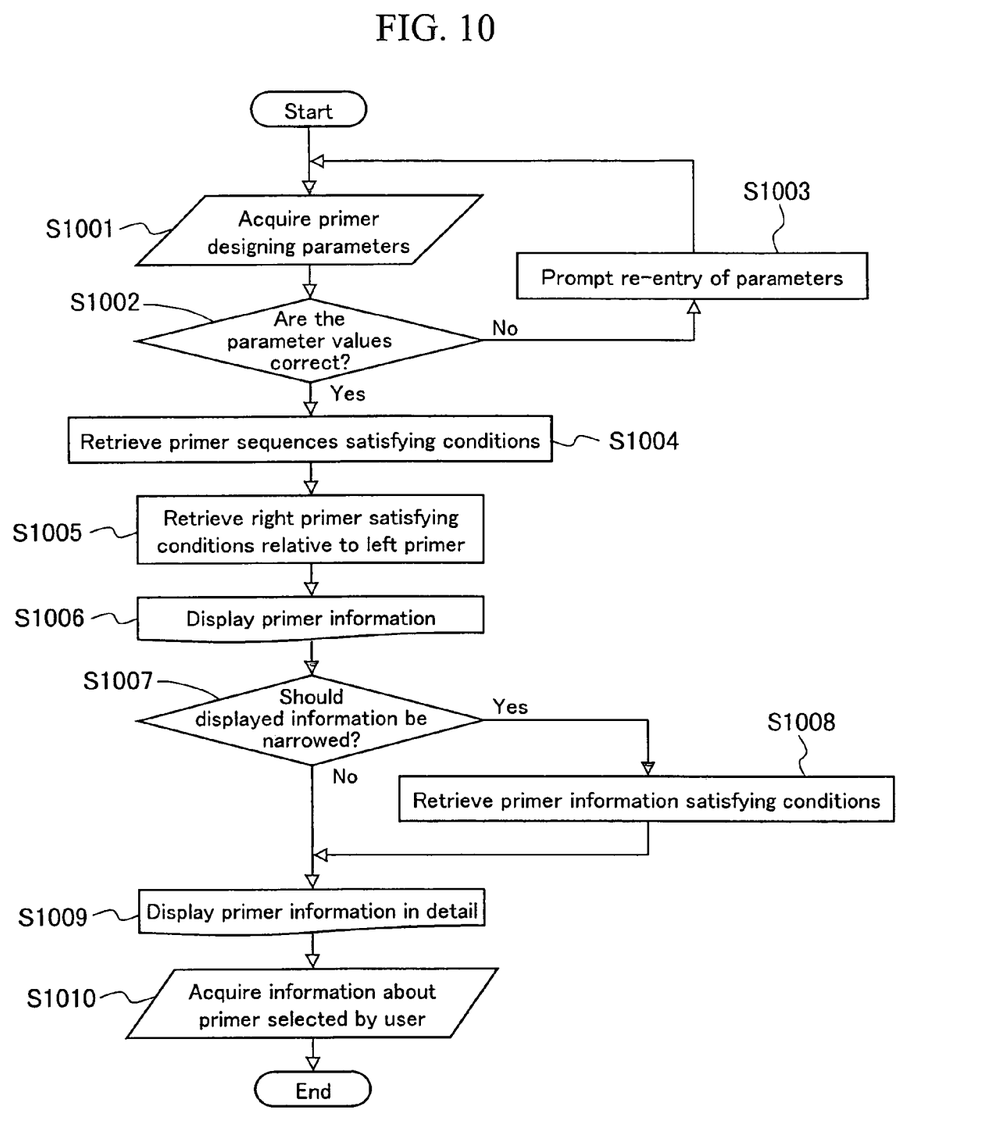
FIG. 10 shows a flowchart of the processes for retrieving a sequence suitable for a primer from a target region.

FIG. 10 shows an outline of the process for retrieving a sequence from a target area at step S805 that is suitable for a primer. This process is carried out by the primer sequence search program 209. At step S1001, the primer designing conditions (parameters) entered in the fields 410, 420, and 430 of FIG. 4 are acquired. At step S1002, it is determined if the parameter values are correct. If they are not correct, the routine advances to step S1003 where a re-entry is prompted. If the parameters are correct, they are delivered to the existing primer search algorithm at step S1004, and a process is carried out to retrieve a sequence suitable as a primer. At step S1005, based on the search result, primers on the nonsense string side with corresponding positional relationship condition relative to a primer on the sense string side are retrieved and grouped into a primer set. At step S1006, the obtained primer information is displayed in the field 602 shown in FIG. 6. At step S1007, it is determined whether or not the displayed information is to be narrowed. Specifically, it is determined whether the refresh button 505 of FIG. 5 has been clicked. If the information is to be narrowed, primer information corresponding to the conditions entered in the field 503 of FIG. 5 is retrieved at step S1008. At step S1009, the detailed information about the corresponding primer set is displayed in the field 602 of FIG. 6. At step S1010, the information about the primer set selected by the user is acquired, which completes the entire process.

While a preferred embodiment of the invention has been described using specific terms, such description is for illustrative purposes only, and it is to be understood that changes and variation may be made without departing from the spirit or scope of the following claims.

What is claimed is:

1. A method for designing a primer for real-time PCR and implemented on a computer suitably configured and programmed to implement said method, comprising:

a file selection step for entering a base sequence data file regarding a target gene;

a determining step for determining whether or not said base sequence data file contains splicing information;

a splicing information calculation step for calculating splicing information if it is determined in said determination step that splicing information is not contained;

a parameter input step for inviting and receiving entries of primer design conditions by displaying splicing information which includes a length of an intron sequence removed by splicing and a position of binding by splicing in a schematic fashion;

a first primer design step for designing primer sets using a known primer search algorithm and in accordance with said primer design conditions and displaying a screen for inviting and receiving entries of conditions for narrowing designed results;

a narrowing step for narrowing the designed results in accordance with said conditions for narrowing designed results if an indication for narrowing designed results is entered into the computer;

a detailed information display step for displaying a detailed information screen which includes a field for displaying said splicing information which includes the length of intron sequence removed by splicing and the position of binding by splicing in a schematic fashion, a field for displaying position information regarding a plurality of primer sets which include a plurality of primers on the nonsense strand side each relative to one primer on sense strand side, and a field for displaying detailed information of primer sets as selected in said field for displaying the position information regarding a plurality of primer sets;

a second primer designing step for designing a primer for preparing an analytical curve-creating template if an indication for designing primer sets for preparing an analytical curve-creating template is entered in the computer; and a primer information output step for output information of the primer sets as designed to a file.

2. The method for designing a primer for real-time PCR according to claim 1, wherein said primer design conditions include the exon numbers on the left and right sides of intron, or the intron number between exons.

3. The computer implemented method for designing a primer for real-time PCR according to claim 1,
wherein the second primer set designing step designs the primer set for preparing a template for creating an analytical curve by performing a known primer search algorithm while excluding an area sandwiched between the selected primer set in said field for displaying detailed information of primer sets in said detailed information screen.

4. The computer implemented method for designing a primer for real-time PCR according to claim 1, wherein the splicing information calculation step involves:

entering a genomic DNA base sequence, while the base sequence being an mRNA base sequence;

processing the base sequence as a character string, substituting an initial value of zero in a variable "DNA position" and a variable "mRNA position," and entering an initial value of zero in a variable "exon number" which counts the number of exons;

substituting ten characters from the "mRNA position" in the mRNA base sequence in a character string "Searched sequence";

retrieving sequences corresponding to the genomic DNA base sequence from the "DNA position," and obtaining all mRNA base sequences included in the genomic DNA base sequence by splicing;

determining whether there is one of the mRNA base sequences corresponding to the base sequence: if no, terminating the splicing information calculation step; if yes, using a subscript of a corresponding letter in the genomic DNA base sequence as a corresponding position, substituting a corresponding letter into a variable "exon start position" and the "DNA position," and incrementing the "exon number", the "mRNA position" and the "DNA position";

comparing letter by letter starting from a letter following the "DNA position" in the genomic DNA base sequence with a letter in the "mRNA position" in the mRNA base sequence, if the letters correspond with each other, incrementing the "mRNA position" and the "DNA positiont";

substituting the "DNA position" into a variable "exon end position," and adding the "exon number," the "exon start position," and the "exon end position" into the splicing information; and determining whether the "mRNA position" is at the end of the mRNA base sequence: if not, returning to the step of substituting ten characters, if yes, outputting the splicing information.

* * * * *

```
SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
actgccatcg gacgtatacc                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
ttcagctaat caagtcaggc                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
caggttacat tacgtcacgg                                                    20
```